US010450555B2

(12) United States Patent
Zheng et al.

(10) Patent No.: US 10,450,555 B2
(45) Date of Patent: Oct. 22, 2019

(54) PREPARATION OF MULTI-HAPTEN MUTANT G6PDH CONJUGATES AND THEIR USE FOR DETECTION OF MULTIPLE ANALYTES

(71) Applicant: Siemens Healthcare Diagnostics Inc., Tarrytown, NY (US)

(72) Inventors: Yi Feng Zheng, Wilmington, DE (US); Yali Yang, Bear, DE (US); Linda Hudson, Rising Sun, MD (US); Nihmat Morjana, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/179,311

(22) Filed: Nov. 2, 2018

(65) Prior Publication Data
US 2019/0055538 A1 Feb. 21, 2019

Related U.S. Application Data

(62) Division of application No. 15/103,572, filed as application No. PCT/US2014/069532 on Dec. 10, 2014, now abandoned.
(Continued)

(51) Int. Cl.
*C12N 9/96* (2006.01)
*C12N 9/04* (2006.01)
(Continued)

(52) U.S. Cl.
CPC .............. *C12N 9/96* (2013.01); *C12N 9/0006* (2013.01); *C12Y 101/01049* (2013.01);
(Continued)

(58) Field of Classification Search
CPC .............. G01N 33/92; G01N 2800/52; G01N 33/6893; G01N 2405/10; G01N 2560/00; G01N 2800/50; G01N 2800/04
See application file for complete search history.

(56) References Cited

U.S. PATENT DOCUMENTS 3,875,011 A 4/1975 Rubenstein et al.
3,905,871 A 9/1975 Rubenstein et al.
(Continued)

FOREIGN PATENT DOCUMENTS

CN 1370994 9/2002
EP 1732880 B1 8/2010

OTHER PUBLICATIONS

Wendt et al., "Evidence for functional convergence of redox regulation in G6PDH isoforms of cyanobacteria and higher plants", 1999, Plant Molecular Biology vol. 40; pp. 487-494.
(Continued)

*Primary Examiner* — Shafiqul Haq
(74) *Attorney, Agent, or Firm* — Cynthia G. Tymeson (57) ABSTRACT

The present invention relates to multi-hapten mutant G6PDH conjugates, methods of their preparation and their use for detection of multiple analytes. The compositions of the invention comprise different types of haptens (molecules) require to be immobilized into the G6PDH to make one multi-hapten-G6PDH conjugate. Both thiol and amine functional groups on G6PDH are utilized for immobilization of different haptens.

9 Claims, 7 Drawing Sheets

Specification includes a Sequence Listing.

Related U.S. Application Data (60) Provisional application No. 61/917,015, filed on Dec. 17, 2013.

(51) Int. Cl.
*G01N 33/535* (2006.01)
*G01N 33/58* (2006.01)

(52) U.S. Cl.
CPC ......... *G01N 33/535* (2013.01); *G01N 33/581* (2013.01); *C07K 2319/00* (2013.01)

(56) References Cited

U.S. PATENT DOCUMENTS

| | | | |
|---|---|---|---|
| 3,975,237 | A | 8/1976 | Rubenstein et al. |
| 5,135,863 | A | 8/1992 | Hu et al. |
| 5,328,828 | A | 7/1994 | Hu et al. |
| 6,033,890 | A * | 3/2000 | Jakobovits ............ C12N 9/0006 435/190 |
| 6,090,567 | A | 7/2000 | Jakobovits et al. |
| 6,455,288 | B1 | 9/2002 | Jakobovits et al. |
| 6,991,911 | B2 | 1/2006 | Zheng et al. |
| 7,022,492 | B2 | 4/2006 | Zheng et al. |
| 7,037,669 | B2 | 5/2006 | Zheng et al. |
| 7,115,383 | B2 | 10/2006 | Zheng et al. |
| 7,560,239 | B2 | 7/2009 | Lin et al. |
| 2003/0224373 | A1 * | 12/2003 | Lin ...................... G01N 33/581 435/6.12 |
| 2006/0046273 | A1 | 3/2006 | Lin et al. |
| 2007/0218506 | A1 | 9/2007 | Zheng et al. |

OTHER PUBLICATIONS

International Search Report and Written Opinion of International Application No. PCT/US2014/069532 dated Jun. 9, 2015.
G-Biosciences; Double-Do Protein Cross-Linkers; Handbook & Selection Guide; G-Biosciences, 2010, [online] [Retrieved on Mar. 17, 2015 by the PCT Officer] <http://wolfson.huji.ac.il/purification/PDF/ProteinInteractions/GBIOSC_ProtCrossLinkersHandbook.pdf> PDF file; pp. 1-16.
Olive et al.,"Glucose 6-Phosphate Dehydrogenase from Leuconostoc mesenteroides", 1971, Kinetic studies; J Biol. Chem.; vol. 246(7); pp. 2047-2057.
Lee et al., "Cloning of the Gene and Amino Acid Sequence for Glucose 6-Phosphate Dehydrogenase from Leuconostoc mesenteroides", 1991, J. Biol. Chem.; vol. 266(20); pp. 13028-13034.
European Search Report and Written Opinion of European Application No. EP 14871809.1 dated Dec. 2, 2016.

\* cited by examiner

PREPARATION OF MULTI-HAPTEN MUTANT G6PDH CONJUGATES AND THEIR USE FOR DETECTION OF MULTIPLE ANALYTES

This is a divisional application of U.S. Ser. No. 15/103,572, filed Jun. 10, 2016 which claims the benefit of U.S. National Stage of International Application No. PCT/US2014/069532, filed Dec. 10, 2014 and claims priority under 35 U.S.C. 119(e) to U.S. Provisional Application No. 61/917,015, filed Dec. 17, 2013. All of the applications are incorporated by reference herein in their entirety.

The present invention relates to multi-hapten mutant G6PDH conjugates, methods of their preparation and their use for detection of multiple analytes.

In the field of in-vitro diagnostics, homogeneous immunoassays, such as Enzyme multiplied immunoassay technique (EMIT)-assays are used to detect analytes, in particular, drugs of abuse in samples of subjects to be tested. For example, the documents U.S. Pat. Nos. 6,455,288, 6,033,890, 6,090,567 describe methods for immunoassay of analytes employing glucose-6-phosphate dehydrogenase (G6PDH) enzymes as labels.

The principle of the EMIT®assay arises from the competitive binding and interaction between an analyte analog conjugate to G6PDH and free analyte in a patient sample to the free antibody. This results in competition between analyte in the sample and analyte- or analyte analog-labeled with glucose-6-phosphate dehydrogenase (G6PDH) for antibody binding sites. The enzyme conjugate activity decreases upon binding to the antibody. The unbound enzyme conjugate converts oxidized nicotinamide adenine dinucleotide (NAD+) in the Antibody Reagent to NADH and the change in the absorbance can be measured spectrophotometrically at 340 nm. Enzyme activity decreases upon binding to the antibody, allowing analyte concentrations in a sample to be measured in terms of G6PDH activity.

EMIT® immunoassays have been developed for screening an individual drug or a class of drugs.

In many cases it is desirable to be able to detect multiple analytes with a single assay. This is relevant e.g. when screening subjects for use of different drugs or simultaneously detecting a drug and its drug metabolites to increase the time window in which drug use can be detected.

U.S. Pat. No. 7,560,239 discloses a composition wherein different analytes are conjugated to G6PDH via amine groups on the G6PDH molecule in a one step reaction. However, conjugating two different analytes to G6PDH via amine chemistry does not allow precise control of the ratio of the two different analytes and may result in loss of enzymatic activity.

OBJECT OF THE INVENTION

The technical problem underlying the present invention is to provide improved G6PDH conjugates, methods of their preparation and their use for detection of multiple analytes.

SUMMARY OF THE INVENTION

Before the invention is described in detail, it is to be understood that this invention is not limited to the particular component parts or the process steps of the methods described as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is also to be understood that plural forms include singular and/or plural referents unless the context clearly dictates otherwise. It is moreover to be understood that, in case parameter ranges are given which are delimited by numeric values, the ranges are deemed to include these limitation values.

The invention relates to a composition which comprises at least two distinct specific binding pair (sbp) members conjugated to a glucose-6-phosphate dehydrogenase (G6PDH), wherein at least a first specific binding pair member is conjugated to G6PDH via a thiol group and wherein at least a further specific binding pair member is conjugated to G6PDH via a amino group.

The composition of the invention can be used to detect both related or similar compounds and unrelated or dissimilar compounds in a homogeneous immunoassay format. For example it could be desired to detect a drug and an analyte of said drug to increase the time window wherein the drug or its metabolite can be detected in a subject. On the other hand it could be desired to simultaneously detect a plurality of unrelated analytes in a single assay, e.g. detection of a variety of drugs for screening a subject for drug abuse. The first and further binding pair can therefore be structuturally similar/related or structurally different/unrelated. Further, the first and further binding pair can be serologically cross-reactive or not cross-reactive.

According to an aspect of the invention, the G6PDH is a mutant G6PDH, the mutant G6PDH being derived from a precursor G6PDH by the insertion of at least one cysteine per subunit, or substitution of at least one amino acid with cysteine per subunit, as compared to the precursor G6PDH.

According to an aspect of the invention, G6PDH is a bacterial G6PDH derived from the genus of bacterium selected from the group consisting of *Leuconostoc*.

Mutant G6PDH which can be used in the compositions and methods of the invention are described in U.S. Pat. Nos. 6,455,288, 6,033,890, and 6,090,567 each of which is herein incorporated by reference in its entirety.

According to an aspect of the invention, the two distinct binding pair members are serologically not cross reactive.

According to an aspect of the invention, the composition comprises three or more distinct specific binding pair (sbp) members conjugated to G6PDH.

According to an aspect of the invention, the composition comprises a plurality of distinct further specific binding pair members conjugated to a respective plurality of amino groups.

According to an aspect of the invention, the composition comprises a plurality of distinct first specific binding pair members conjugated to a respective plurality of thiol groups.

According to an aspect of the invention, the first and second specific binding pair members are selected from the group consisting of opium, opioid analgesics, amphetamines, cocaine, methadone, alkaloids, catecholamines, methylendioxyamphetamines (MDMA, MDA, and MDEA, etc.), PCP, propoxyphene, methaqualone, barbiturates, benzodiazepines, tricyclic antidepressants, tranquilizers, tetrahydrocannabinol, LSD, ketamine, GHB, and other drugs of abuse, including amino acids, hormones, and steroids, buprenorphine, norbuprenorphine, and analogs, metabolites, and derivatives thereof.

According to an aspect of the invention, the composition comprises a linker between G6PDH and either or both of specific binding pair member and further specific binding pair member.

The linker usually comprises a chain of 1, 2, 3, 4, 5, 6, 7, 8, 9, 10, 11, or 12 atoms, e.g., from about 3 to about 8 atoms, or e.g. from about 4 to about 7 atoms, each independently selected from the group normally consisting of carbon, oxygen, sulfur, nitrogen, halogen and phosphorous, and so forth. The linking group may be aliphatic or aromatic. When heteroatoms are present, oxygen will usually be present as oxo or ether bonded to carbon; sulfur is usually present as a thioether or other functionality that corresponds to an analogous oxygen functionality; nitrogen is usually present as nitro, nitroso or amino, normally bonded to carbon; phosphorous is usually bonded to carbon, sulfur, oxygen or nitrogen, usually as phosphonate and phosphate mono- or diester. Common functionalities in forming a covalent bond between the linker and the molecule to be conjugated, namely, enzyme or analyte, include alkylamine, amidine, thioamide, ether, urea, thiourea, halogen, isothiocyanate, guanidine, azo, thioether and carboxylate, sulfonate, and phosphate esters, amides and thioesters.

The invention further relates to a method for producing a composition of the invention, comprising the steps of:

conjugating a first specific binding pair member to G6PDH via a thiol group; and then conjugating at least a further specific binding pair member to G6PDH via a amino group.

According to an aspect of the invention, the step of conjugating includes providing a linker between G6PDH and either or both of specific binding pair member and further specific binding pair member.

The invention further relates to a method of detecting a first analyte and a further analyte in a sample, comprising the steps of:

(i) combining in a liquid medium:
  (a) said sample,
  (b) a composition comprising G6PDH wherein a first specific binding pair member is conju-gated to G6PDH via a thiol group and a further specific binding pair member is conjugated to G6PDH via an amino group,
  (c) a first antibody capable of binding the first specific binding pair member,
  (d) a further antibody capable of binding the further specific binding pair member, and
  (e) a substrate for said G6PDH; and (ii) determining the enzymatic activity of said G6PDH in said medium.

Enzymatic activity can be determined by using a suitable signal producing system.

The analytes of interest include, but are not limited to drugs, metabolites, pesticides, pollutants, and the like. Included among drugs of interest are the alkaloids. Among the alkaloids are morphine alkaloids, which includes morphine, codeine, heroin, dextroamphetamine, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites. Analytes of particular interest include opium, opioid analgesics, amphetamines, cocaine, methadone, alkaloids, catecholamines, methylendioxyamphetamines (MDMA, MDA, and MDEA, etc.), PCP, propoxyphene, methaqualone, barbiturates, benzodiazepines, tricyclic antidepressants, tranquilizers, tetrahydrocannabinol, LSD, ketamine, GHB, and other drugs of abuse, including amino acids, hormones, and steroids, buprenorphine, norbuprenorphine, and analogs, metabolites, and derivatives thereof.

Definitions

Before proceeding further with the description of the specific embodiments of the invention, a number of terms will be defined. Unless defined otherwise, technical and scientific terms used herein have the same meaning as commonly understood by one of ordinary skill in the art to which this invention belongs.

In the context of the present invention, an analyte is a compound or composition to be measured, the material of interest. The analyte is a member of a specific binding pair (sbp) and may be a ligand, which is mono- or polyvalent, usually antigenic or haptenic, and is a single compound or plurality of compounds which share at least one common epitopic or determinant site.

In the context of the present invention, a sample which is reasonably suspected of containing analyte can be analyzed by the method of the present invention. Such samples can include human, animal or man-made samples. The sample can be prepared in any convenient medium which does not interfere with the assay. Typically, the sample is an aqueous solution or a natural fluid, preferably, urine, whole blood, serum, plasma, cerebral-spinal fluid, or saliva more preferably, serum. The sample source can also be hair or tissue.

The term glucose-6-phosphate dehydrogenase or "G6PDH" refers to the enzyme glucose-6-phosphate dehydrogenase, which may be obtained either from natural sources, such as from yeast, bacteria, in native or mutational form or prepared by recombinant methods.

A "precursor G6PDH" means a naturally occurring G6PDH enzyme as well as a recombinant G6PDH enzyme having a sequence substantially identical to a naturally occurring G6PDH.

The amino acid sequence of a G6PDH mutant is derived from the precursor G6PDH amino acid sequence by the substitution or deletion of one or more amino acids of the precursor amino acid sequence or the insertion of one or more amino acids into the precursor amino acid sequence. Such modification can be achieved by recombinant modification of the precursor DNA sequence which encodes the amino acid sequence of the precursor G6PDH rather than manipulation of the precursor G6PDH enzyme per se. The techniques of DNA recombinant engineering are known in the art.

In the context of the present invention, measuring the amount of an analyte comprises quantitative, semiquantitative, and qualitative methods as well as all other methods for determining analyte. For example, a method which merely detects the presence or absence of analyte in a sample suspected of containing an analyte is considered to be included within the scope of the present invention. Synonyms for the phrase "measuring the amount of analyte" which are contemplated within the scope of the present invention include, but are not limited to, detecting, measuring, or determining analyte; detecting, measuring, or determining the presence of analyte; and detecting, or determining the amount of analyte.

In the context of the present invention, a member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, or the like. These will usually be members of an immunological pair such as antigen-antibody.

A ligand is any organic compound for which a receptor naturally exists or can be prepared. For example, in one context of the present invention, the analyte is a ligand and the present invention provides methods for determining the concentration of the analyte which is a ligand.

An analog of a ligand, of an analyte or of a member of a specific binding pair (sbp member) is modified ligand or ligand surrogate, modified analyte or analyte surrogate, or modified sbp member or sbp member surrogate which can compete with the analogous ligand, analyte or sbp member for a receptor, antiligand, sbp partner, or the like, the modification providing means to join a ligand analog, analyte analog, or sbp member analog to another molecule. The ligand analog, analyte analog, or sbp member analog will usually differ from the ligand, analyte, or sbp member by more than replacement of a hydrogen with a bond which links the ligand analog, analyte analog, or sbp member analog to a hub or label, but need not.

A receptor is any compound or composition capable of recognizing a particular spatial and polar organization of a molecule. These organized areas of a molecule are referred to as epitopic or determinant sites. Illustrative naturally occurring receptors include antibodies and enzymes.

A linker or a linking group is a portion of a structure which connects 2 or more substructures. A linking group has at least 1 uninterrupted chain of atoms extending between the substructures. The atoms of a linking group are themselves connected by chemical bonds.

A conjugate is a molecule comprised of two or more substructures bound together, optionally through a linking group, to form a single structure. The binding can be made either by a direct connection (e.g. a chemical bond) between the subunits or by use of a linking group. Within the context of the present invention, a conjugate is a G6PDH enzyme attached to a hapten, sbp member or analyte analog.

Conjugation is any process wherein two moieties, chemical structures, or molecules are linked together to form a conjugate. The conjugation process can be comprised of any number of steps.

Haptens are capable of binding specifically to corresponding antibodies, but usually do not themselves act as immunogens for preparation of the antibodies. Antibodies which recognize a hapten can be prepared against compounds comprised of the hapten linked to an immunogenic carrier.

The signal producing system is utilized in assays for analytes and may have one or more components, at least one component being a mutant G6PDH. The signal producing system generates a signal that relates to the presence or amount of analyte in a sample. The signal producing system includes all of the reagents required to produce a measurable signal.

Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like.

The signal producing system provides a signal detectable by external means, normally by measurement of electromagnetic radiation, desirably by visual examination. For the most part, the signal producing system includes a chromophoric substrate and mutant G6PDH enzyme of the invention, where chromophoric substrates are enzymatically converted to dyes which absorb light in the ultraviolet or visible region.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

INCORPORATION BY REFERENCE

All publications and patent applications cited herein are incorporated by reference as if each individual publication or patent application were specifically and individually indicated to be incorporated by reference.

DETAILED DESCRIPTION OF THE INVENTION

Additional details, features, characteristics and advantages of the object of the invention are further disclosed in the following description and figures of the respective examples, which, in an exemplary fashion, show preferred embodiments of the present invention. However, these examples should by no means be understood as to limit the scope of the invention.

In the attached Figures,

FIG. 8 shows a response curve for detection of ecstasy, MDA, MDEA, methamphetamine and amphetamine using a composition according to the invention, Homogeneous enzyme immunoassays depend on the availability of enzyme-sbp member conjugates whose enzyme activity can be strongly modulated on binding of the sbp partner. The present invention provides enzyme-sbp member conjugates which can bind to and detect multiple different analytes for conducting assays that are useful in homogeneous immunoassays.

The compositions of the invention with multiple detection capability in EMIT®format need to satisfy some basic conditions: 1) different types of haptens (molecules) require to be immobilized into the G6PDH to make one multi-hapten-G6PDH conjugate; 2) the multi-hapten-G6PDH conjugate needs to be recognized by its corresponding antibody (ies) in order to generate enzymatic inhibition and therefore detection of multiple drugs; 3) the multi-hapten-G6PDH conjugate should retain its enzymatic activity. Based on these conditions, mutant G6PDH was selected as an excellent template to make the new multi-hapten-G6PDH conjugate. Both thiol and amine functional groups on G6PDH are utilized for immobilization of different haptens.

A suitable mutant G6PDH for example is G6PDH from *Leuconostoc mesenteroides* (e.g. ATCC 12291) carrying one or several of the following mutations:
Ala-45-Cys
Arg-46-Cys
Gln-47-Cys
Ala-48-Cys
Leu-49-Cys
Asn-50-Cys
Asp-51-Cys
Asp-52-Cys
Glu-53-Cys
Phe-54-Cys
Lys-55-Cys
Gln-56-Cys
Leu-57-Cys
Val-58-Cys
Arg-59-Cys
Asp-60-Cys
Lys-128-Cys
Lys-182-Cys The entire amino acid sequence of the wild type G6PDH from *Leuconostoc mesenteroides* is given below and in references 12, 13, and 14:

```
VSEIKTLVTF FGGTGDLAKR KLYPSVFNLY KKGYLQKHFA

IVGTARQALN DDEFKQLVRD SIKDFTDDQA QAEAFIEHFS

YRAHDVTDAA SYAVLKEAIE EAADKFDIDG NRIFYMSVAP

RFFGTIAKYL KSEGLLADTG YNRLMIEKPF GTSYDTAAEL

QNDLENAFDD NQLFRIDHYL GKEMVQNIAA LRFGNPIFDA

AWNKDYIKNV QVTLSEVLGV EERAGYYDTA GALLDMIQNH

TMQIVGWLAM EKPESFTDKD IRAAKNAAFN ALKIYDEAEV

NKYFVRAQYG AGDSADFKPY LEELDVPADS KNNTFIAGEL

QFDLPRWEGV PFYVRSGKRL AAKQTRVDIV FKAGTFNFGS

EQEAQEAVLS IIIDPKGAIE LKLNAKSVED AFNTRTIDLG

WTVSDEDKKN TPEPYERMIH DTMNGDGSNF ADWNGVSIAW

KFVDAISAVY TADKAPLETY KSGSMGPEAS DKLLAANGDA WVFKG
```

In analogy, further suitable mutant forms of G6PDH are derived from other strains of *Leuconostoc mesenteroides*, from strains of *Leuconostoc citreum* (e.g. strain NCIMB 3351), *Leuconostoc lactis* (e.g. strain NCDO 546), and *Leuconostoc dextranicum* (e.g. strain ATCC 19255). Suitable mutations include the insertion of at least one cysteine per subunit, or substitution of at least one amino acid with cysteine per subunit, as compared to the precursor G6PDH. In particular, suitable mutant forms of G6PDH include mutations wherein a respective amino acid in a precursor G6PDH molecule derived from *Leuconostoc* is substituted by cystein at any of the positions 45 to 60.

Figure 1:
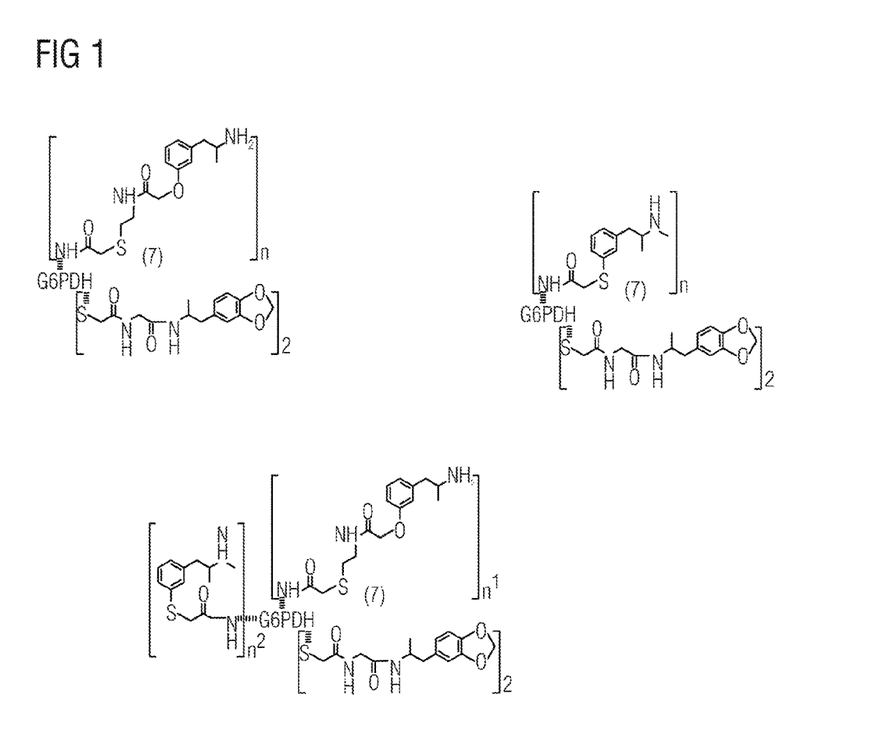
FIG. 1 schematically shows the chemical structure of embodiments of compositions according to the invention.
Figure 2:
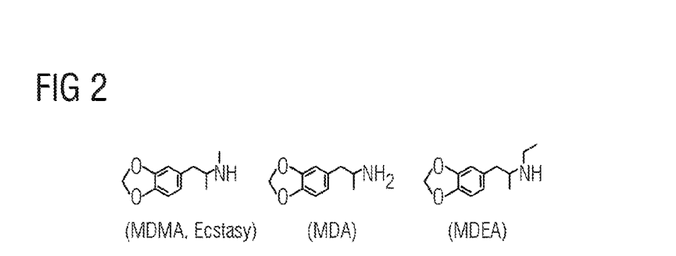
FIG. 2 shows the structure of the exemplary analytes MDMA, MDA and MDEA.
Figure 3:
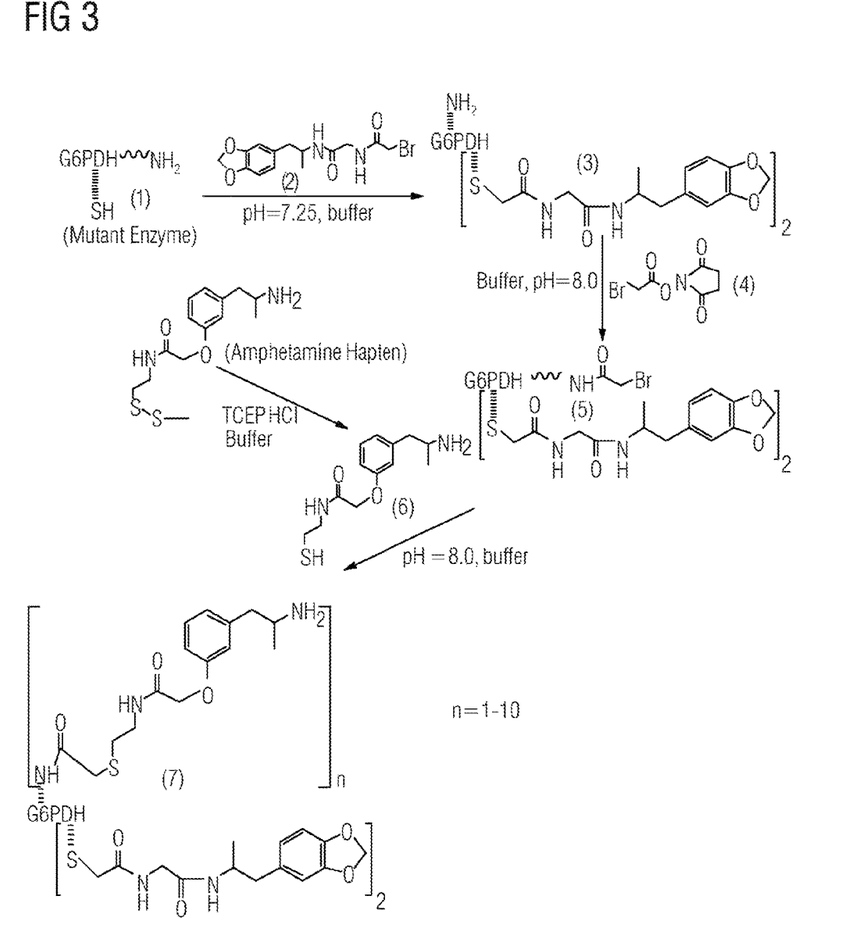
FIG. 3 shows an exemplary synthesis scheme for obtaining an embodiment of a composition according to the invention, showing the synthesis of MDA/amphetamine mutant G6PDH conjugate (7)
Figure 4:
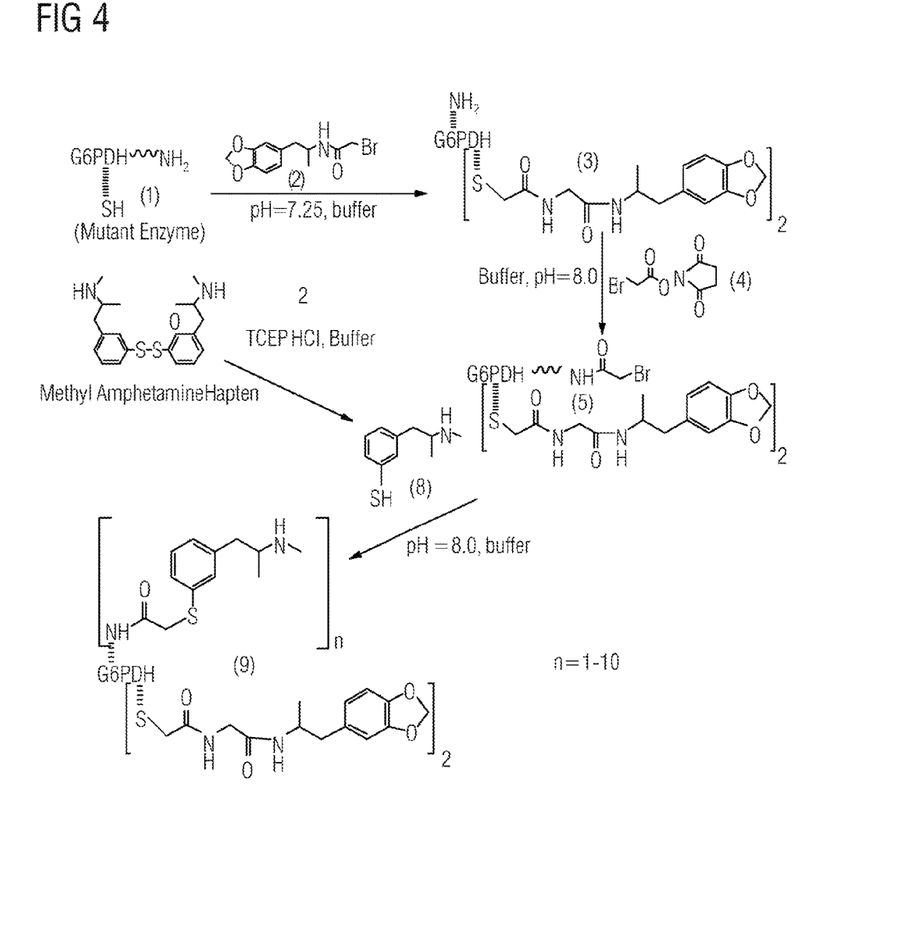
FIG. 4 shows an exemplary synthesis scheme for obtaining an embodiment of a composition according to the invention, showing the synthesis of MDA/Methamphetamine mutant G6PDH conjugate (9)
Figure 5:
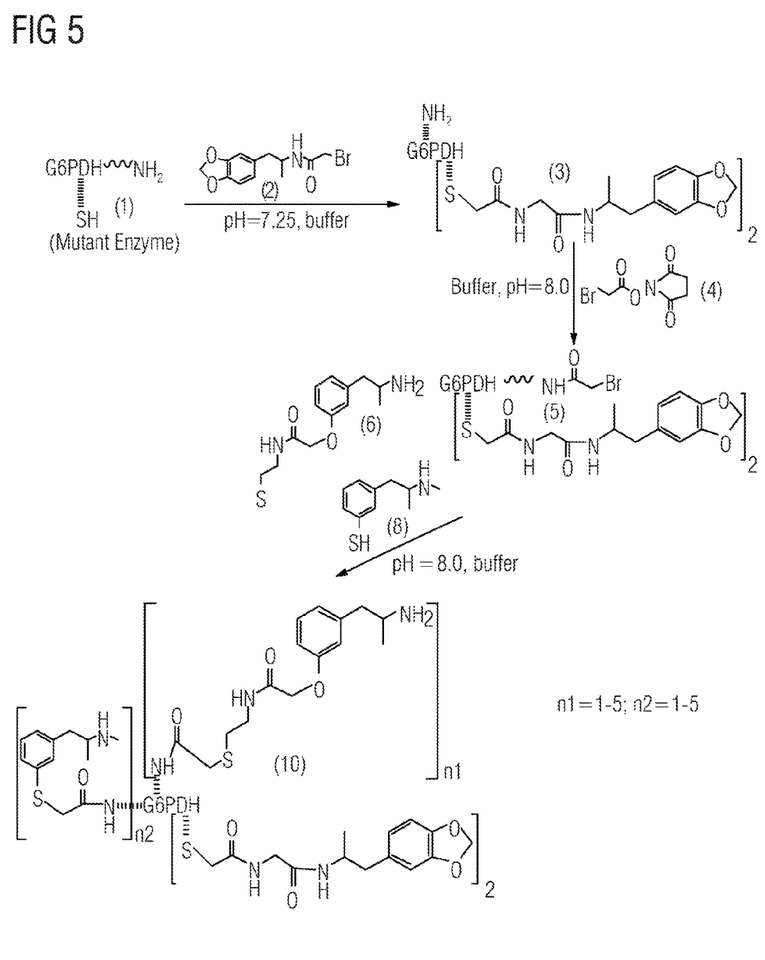
FIG. 5 shows an exemplary synthesis scheme for obtaining an embodiment of a composition according to the invention, showing the synthesis of MDA/Amphetamine/Methamphetamine mutant G6PDH conjugate (10)

The reagent formulation is a two-step reaction. First, two haptens are attached to the G6PDH (Schemes 1-3) using the thiol chemistry in a controlled manner. Second, different types of haptens can be immobilized using the amine chemistry. Our approaches are different from that of the existing multi-hapten conjugate (reference 11) in which only amine chemistry was used. Based on existing data, using the amine functional groups for immobilization of haptens could lead to reduction of the enzymatic activity. This means that only limited amine groups can be used for the attachment of haptens in order to maintain good enzymatic activity for the EMIT®format. Consequently, using amine chemistry only for preparation of multi-hapten-G6PDH conjugate could limit the amount of hapten on the conjugate in order to maintain good enzymatic activity.

In our approaches, multi-hapten-mutant G6PDH was prepared using the thiol function groups on the enzyme as the first step reaction. The resulting conjugate retains most of its enzymatic activity (≥95%). This could be an advantage in that more haptens can be attached to the amine groups in the second step reaction, while still maintaining good enzymatic activity. Therefore, applying both thiol and amine chemistry in preparation of multi-hapten-G6PDH should result in a conjugate that has more hapten loading capacity for the detection of multiple analytes. Without wishing to be bound by this theory, the beneficial effect of utilizing thiol chemistry in thee compositions and methods of the invention could be explained as follows: Utilization of thiol chemistry to could result in more stable. Cystein residues can be used that are distanced from the active site of the enzyme e. In that regard, hapten conjugation through linkage of cysteine may have little or no impact on the stability of the active quaternary structure that is crucial for the enzymatic activity. This is supported by the observation that mutant G6PDH-hapten conjugates retain very good enzymatic.

There are many analytes, e.g. drugs, that can be used to prepare multi-hapten-G6PDH and test its performance. Three widely abused drugs, amphetamine, methamphetamine and ecstasy were selected as exemplary analytes. With this in mind, multi-hapten-G6PDH (7, 9, 10) was prepared as described in Schemes 1-3 and the experimental section. Two multi-hapten-G6PDHs (7, 9) were used to investigate their multi-drug detection capability in the EMIT® format. Results were discussed in the following section.

In these approaches, multi-hapten-mutant G6PDH was prepared using the thiol function groups on the enzyme as the first step reaction. The resulting conjugate retains most of its enzymatic activity (≥95%). This could be an advantage in that more haptens can be attached to the amine groups in the second step reaction, while still maintaining good enzymatic activity. Therefore, applying both thiol and amine chemistry in preparation of multi-hapten-G6PDH should result in a conjugate that have more hapten loading capacity for the detection of multiple analytes.

EMIT®Assay Principle:

The Emit® II Plus Assay is a homogeneous enzyme immunoassay. It is based on competition between drug in the sample and drug-labeled with glucose-6-phosphate dehydrogenase (G6PDH) for antibody binding sites. The enzyme conjugate activity decreases upon binding to the antibody. The unbound enzyme conjugate converts the oxidized nicotinamide adenine dinucleotide (NAD) in the Antibody Reagent to NADH and the change in the absorbance can be measured spectrophotometrically at 340 nm. Enzyme activity decreases upon binding to the antibody, allowing analyte concentrations in a sample to be measured in terms of G6PDH activity.

Testing is carried out using the SYVA®D30-R analyzer Syva-30R, S/N A3562011, available from Siemens Healthcare Diagnostics Inc., Newark Del. The instrument is employed using EMIT® immunoassay technology. In the embodiment of the EMIT® method used herein and discussed in more detail below, competition between ecstasy and/or amphatemine/methamphetamine analogs on G6PDH conjugates and free drugs in patient samples for antibody binding sites is utilized to determine the amount of ecstasy and/or amphetamine/methamphetamine in patient samples. The enzymatic activity of the free conjugate is measured and is directly proportional to the amount of drugs in the patient sample.

Figure 6:
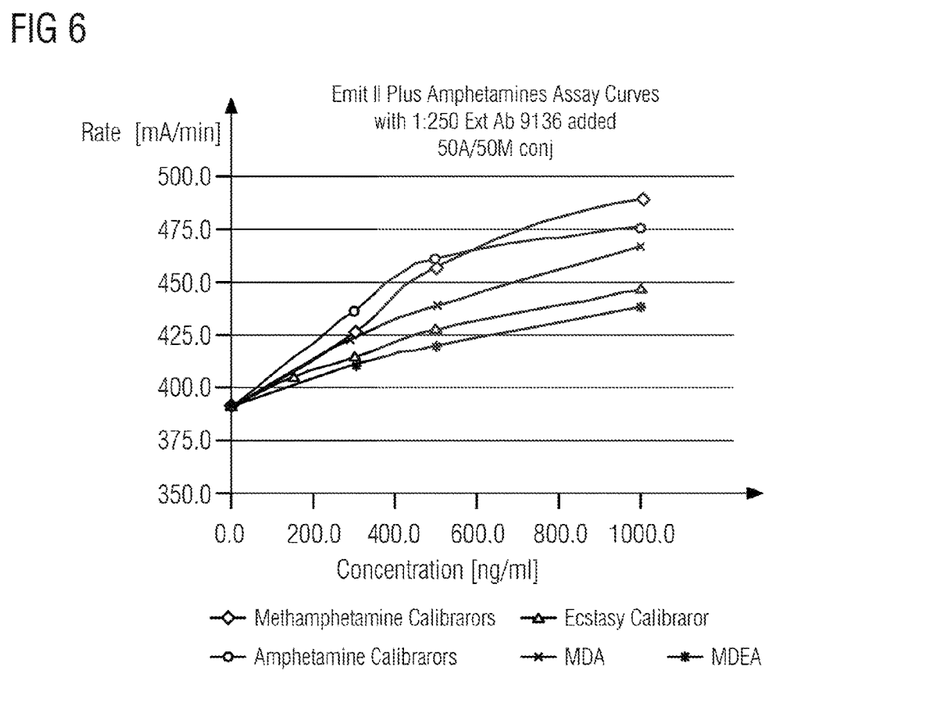
FIG. 6 shows a response curve for detection of ecstasy, MDA, MDEA, methamphetamine and amphetamine using a composition according to the invention.
Figure 7:
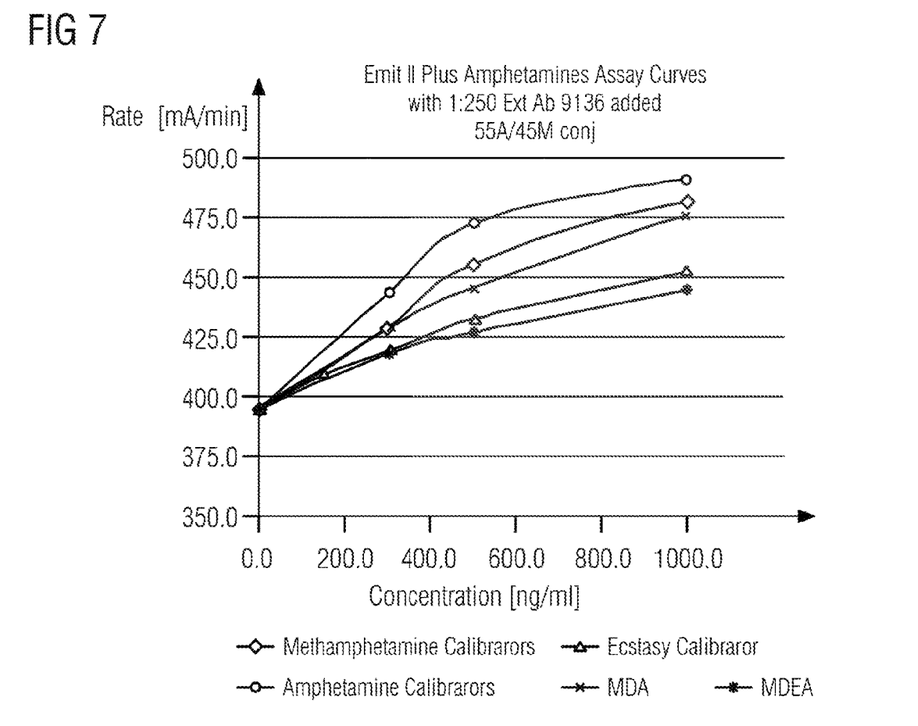
FIG. 7 shows a response curve for detection of ecstasy, MDA, MDEA, methamphetamine and amphetamine using a composition according to the invention.
Figure 8:
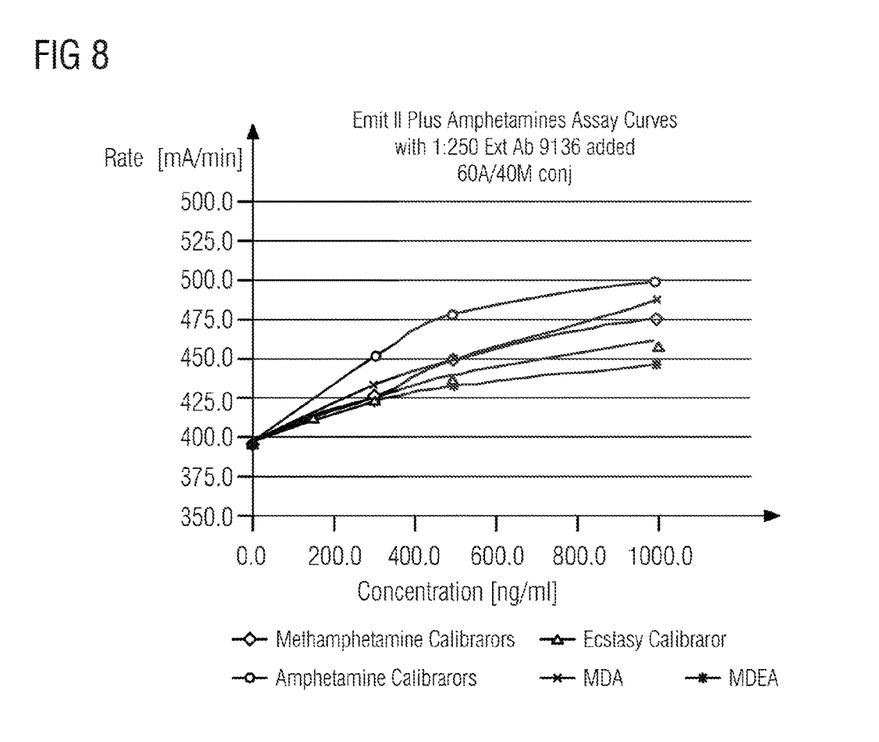

EMIT®Assay Results:

Conclusion: Multi-hapten G6PDH conjugates (7, 9, 10) were successfully prepared using mutant G6PDH with both thiol and amine chemistry. The multi-hapten conjugates (7, 9) were used to produce response curves for the multianalyte of Amphetamine, Methamphetamine, MDMA, MDE and MDEA. The response for each drug can be modulated by changing the conjugate ratios. This concept can be applied to any multi-analyte detection format including EMIT®format.

Experimental Section:

Reagents

1) Antibody Reagent: The amphetamine, methamphetamine and Ecstasy antibodies were formulated in the antibody reagent 1 diluent by spiking at concentrations of 45 ug·mL, 7 ug/mL and (1:250) respectively.

2) Conjugate reagent 2: Conjugate lot #7 and #9 (50:50) were formulated separately in the reagent 1 diluent at an Rmax of 750 mA/min. The conjugate solutions were mixed at different ratios (Vol:Vol).

3) Standards/Calibrators: Amphetamines, Methamphetamines, Ecstasy (MDMA), MDA and MDEA standards were prepared at concentrations of 0-1000 ng/mL 4) Protocol:
Antibody reagent 1=210 uL,
Conjugate Reagent 2=90 uL
Sample size=5 uL
First Wavelength: 340 nm
Second Wavelength: 412 nm
Instrument: Syva-30-R Analyzer S/N A3562011
Preparation of Mutant G6PDH (1)
The mutant G6PDH (1) were invented and prepared as described in references 1-3.

Preparation of Mutant MDA-G6PDH Conjugate (3)

The hapten (2) and its mutant G6PDH Conjugate (3) were prepared as described in reference 4.

Preparation of MDA/Amphetamine Mutant G6PDH Conjugate (7)

Functionization of G6PDH Conjugate (3)

MDA-G6PDH conjugate (3) in pH 7.0 sodium phosphate buffer (5 mL at 1 mg/mL) is buffer exchanged in a stirred ultrafiltration cell (10 mL) with 55 mM Tris.HCl, pH 8.0 buffer three times. Final enzyme collected is 1.0 mL with a concentration of 5.0 mg/mL. To buffer exchanged G6pDH conjugate in 4° C. are added D-glucose 6-phosphate disodium salt hydrate (Sigma, G7250, 30 mg) and NADH (β-NADH disodium salt, USB, Cat. 15345, 30 mg), pH of the solution is checked and found to be 8. To this solution is added 50 µL succinimidyl bromoacetate (4, Molecular Bioscience, Cat. 22080, mw: 237.0, 5 mg/mL in DMF) in an ice-water bath. The enzyme solution is stirred in cold room for 45 minutes then dialyzed with 1 L of 55 mM Tris HCl, pH 8.0 buffer, exchanged with fresh buffer five times with three hours between each fresh buffer. The dialyzed enzyme solution (5) collected is 2.1 mL with a concentration of 2.45 mg/mL.

Reduction of Amphetamine Hapten Linker with TCEP 30 mL of carbitol (Diethylene glycol monoethyl ether, Sigma, D1265-1L) and 20 mL of 20 mM of Sodium acetate pH 4.5 buffer are degassed by bubbling nitrogen through each solution for 15 minutes before the addition of amphetamine hapten. To amphetamine hapten (MW 314.47, 10.4 mg) in a small flask are added degassed carbitol (0.4368 ml) and sodium actate (20 mM, pH 4.5, 0.2184 mL). The reaction mixture is stirred under nitrogen atmosphere. TCEP HCl (Sigma, C4706, MW 286.65, 11.8 mg, 1.24 equivalent of amphetamine hapten) is added into amphetamine hapten solution. The progress of the reaction is monitored by TLC (10.5 ml $CH_2Cl_2$/4 mL MeOH/0.25 mL acetic acid) and product (6) is a spot less polar than that of amphetamine hapten and stained bright yellow with Ellman's Reagent. The reaction finishes within one hour.

MDA G6PDH Conjugatate with Amphetamine

MDA-G6PDH deactivated conjugate (5) is bubbled with nitrogen for 30 minutes in an ice-water bath, amphetamine-SH hapten (6, 117 µL) is added into the conjugate in an ice water bath drop wise through a syringe under nitrogen atmosphere. The reaction mixture is stirred in a cold room overnight. MDA-G6PDH-amphetamine conjugate is loaded onto a pre-equilibrated G-50 Sephadex column with 55 mM Tris HCl buffer (0.1% $NaN_3$, pH 8.0), eluted with same buffer. Fractions containing the conjugate (7) are pooled and concentration of the protein is determined by UV at 280 nm. The concentration of the conjugate (7) is determined to be 0.43 mg/ml (11.7 mL) by absorbance at 280 nm.

Preparation of MDA/Methamphetamine Mutant G6PDH Conjugate (9):

Functionization of G6PDH Conjugate (3)

MDA-G6PDH conjugate (3) in pH 7.0 sodium phosphate buffer (4.6 mL at 1 mg/mL) is buffer exchanged in a stirred ultra-filtration cell (10 mL) with 55 mM Tris.HCl, pH 8.0 buffer three times. Final enzyme collected is 0.9 mL with a concentration of 5.0 mg/mL. To buffer exchanged G6pDH conjugate in 4° C. are added D-glucose 6-phosphate disodium salt hydrate (Sigma, G7250, 27.6 mg) and NADH (β-NADH disodium salt, USB, Cat. 15345, 27.6 mg), pH of the solution is checked and found to be around 8. To this solution is added 46.0 µL succinimidyl bromoacetate (4, Molecular Bioscience, Cat. 22080, mw: 237.0, 5 mg/mL in DMF) in an ice-water bath. The enzyme solution is stirred in cold room (4° C.) for 45 minutes and dialyzed with 1 L of 55 mM Tris HCl, pH 8.0 buffer, exchanged with fresh buffer five times with three hours between each fresh buffer. Dialyzed enzyme solution (5) collected is 2.5 mL with a concentration of 2.44 mg/mL.

Reduction of Methyl Amphetamine Hapten Linker with TCEP 30 mL of carbitol (Diethylene glycol monoethyl ether, Sigma, D1265-1L) and 20 mL of 20 mM of Sodium acetate pH 4.5 buffer are degassed by bubbling nitrogen through for 15 minutes before the addition of methyl amphetamine hapten. To methyl amphetamine hapten (MW 360.58, 11.9 mg) in a small round bottomed flask are added degassed carbitol (0.4998 ml) and sodium acetate (20 mM, pH 4.5, 0.2499 mL). The reaction mixture is stirred under nitrogen atmosphere. TCEP HCl (Sigma, C4706, MW 286.65, 12.77 mg, 1.35 equivalent of methyl amphetamine hapten) is added into the methyl amphetamine hapten solution. The progress of the reaction is monitored by TLC (10.5 ml $CH_2Cl_2$/4 mL MeOH/0.25 mL acetic acid) and product (8)

is a spot less polar than that of methyl amphetamine hapten and stained bright yellow with Ellman's Reagent. The reaction finishes in one hour.

MDA G6PDH Conjugate with Methyl amphetamine

MDA-G6PDH deactivated conjugate (5, 2.25 mL) is bubbled with nitrogen for 30 minutes in an ice-water bath, methyl amphetamine-SH hapten (8, 155 µL) is added into the conjugate in an ice water bath drop wise through a syringe under nitrogen atmosphere. The reaction mixture is stirred in a cold room (4° C.) overnight. MDA-G6PDH-methyl amphetamine conjugate is loaded onto a pre-equilibrated G-50 Sephadex column with 55 mM Tris HCl buffer (0.1% $NaN_3$, pH 8.0), eluted with same buffer. Fractions containing the conjugate (9) are pooled and the concentration of the protein is determined to be 0.48 mg/ml (8.88 ml) by UV at 280 nm.

Preparation of MDA/Amphetamine/Methamphetamine Mutant G6PDH Conjugate (10):

Functionization of G6PDH Conjugate (3)

MDA-G6PDH conjugate (3) in sodium pH 7.0 phosphate buffer (15 mL at 1 mg/mL) is buffer exchanged in a stirred ultra-filtration cell (50 mL) with 55 mM Tris.HCl, pH 8.0 buffer three times. Final enzyme collected is 3.0 mL with a concentration of 5.0 mg/mL. To buffer exchanged G6pDH conjugate in 4° C. are added D-glucose 6-phosphate disodium salt hydrate (Sigma, G7250, 90.2 mg) and NADH (β-NADH disodium salt, USB, Cat. 15345, 90.1 mg), pH of the solution is checked and found to be around 8. To this G6PDH conjugate solution is added 150.0 µL succinimidyl bromoacetate (4, Molecular Bioscience, Cat. 22080, mw: 237.0, 5 mg/mL in DMF) in an ice-water bath. The solution is stirred in cold room (4° C.) for 45 minutes. The enzyme solution is dialyzed with 1 L of 55 mM Tris HCl, pH 8.0 buffer, exchanged with fresh buffer five times with three hours between each fresh buffer. Dialyzed enzyme solution (5) collected is 6.7 mL with a concentration of 4.52 mg/mL.

Reduction of Methyl Amphetamine/Amphetamine Hapten Linkers with TCEP 30 mL of carbitol (Diethylene glycol monoethyl ether, Sigma, D1265-1L) and 30 mL of 20 mM of Sodium acetate pH 4.5 buffer are degassed by bubbling nitrogen through for 15 minutes before the addition of hapten. To methyl amphetamine hapten (MW 360.58, 10.4 mg) in a small round bottomed flask are added degassed carbitol (0.4368 ml) and sodium acetate (20 mM, pH 4.5, 0.2184 mL). The reaction mixture is stirred under nitrogen atmosphere. TCEP HCl (Sigma, C4706, MW 286.65, 11.16 mg, 1.35 equivalent of methyl amphetamine hapten) is added into methyl amphetamine hapten solution. The progress of the reaction is monitored by TLC (10.5 ml $CH_2Cl_2$/4 mL MeOH/0.25 mL acetic acid) and product (8) is a spot less polar than that of methyl amphetamine hapten and stained bright yellow with Ellman's Reagent. The reaction finishes in one hour. At the same time, to amphetamine hapten (MW 314.47, 7.5 mg) in a small round bottomed flask are added degassed carbitol (0.3150 mL) and NaOAc (20 mM, pH 4.5, 0.1575 mL). The solution is stirred under nitrogen atmosphere; TCEP HCl (Sigma, C4706, MW 286.65, 9.23 mg, 1.35 equivalent of amphetamine hapten) is added into amphetamine hapten solution. The progress of the reaction is monitored by TLC (10.5 ml $CH_2Cl_2$/4 mL MeOH/0.25 mL acetic acid) and product (6) is a spot less polar than that of methyl amphetamine hapten and stained bright yellow with Ellman's Reagent. The reaction finishes in one hour.

MDA G6PDH Conjugate with Methyl amphetamine and Amphetamine

MDA-G6PDH deactivated conjugate (5, 1.8 mL, 4.52 mL) is bubbled with nitrogen for 30 minutes in an ice-water bath, methyl amphetamine-SH hapten (8, 65.5 µL) and amphetamine-SH hapten (6, 57.1 µL) (molar ratio of methyl amphetamine hapten and amphetamine hapte is 1 to 1) are added into the MDA G6PDH deactivated conjugate in an ice water bath drop wise through a syringe under nitrogen atmosphere. The reaction mixture is stirred in a cold room overnight. MDA-G6PDH-methyl amphetamine/methyl amphetamine conjugate is loaded onto a pre-equilibrated G-50 Sephadex column with 55 mM Tris HCl buffer (0.1% $NaN_3$, pH 8.0), eluted with same buffer. Fractions containing the conjugate (10) are pooled and concentration of the protein is determined to be 0.44 mg/ml (11.8 ml) by UV at 280 nm.

REFERENCES

1. Jakobovits et al. U.S. Pat. No. 6,033,890 "Homogeneous immunoassay using mutant glucose-6-phosphate dehydrogenases" Issued: Mar. 7, 2000
2. Jakobovits et al. U.S. Pat. No. 6,090,567 "Homogeneous immunoassay using mutant glucose-6-phosphate dehydrogenases" Issued: Jul. 18, 2000.
3. Jakobovits et al. U.S. Pat. No. 6,455,288 "Homogeneous immunoassay using mutant glucose-6-phosphate dehydrogenases" Issued: Sep. 18, 2002.
4. Zheng, Y. F.; Liu, H. T. "Assay For Entactogens" U.S. Pat. No. 6,991,911, 2006.
5. Zheng, Y. F.; Yang, Y. "Ecstasy Haptens And Immunogens" U.S. Pat. No. 7,022,492, 2006.
6. Zheng, Y. F.; Parrish, F. R.; Valdez, J.; Liu, H. T. "Assays For Amphetamine and Methamphetamine" European. Patent No. 1732880, 2010.
7. Zheng, Y. F.; Parrish, F. R.; Valdez, J.; Liu, H. T. "Assays For Amphetamine and Methamphetamine" U.S. Pat. No. 7,115,383, 2006.
8. Zheng, Y. F.; Yamout, A. K.; Berger, E. D.; Hu, W. M.; Liu, H. T. "Assays For Amphetamine and Methamphetamine Using Stereospecific Reagents" U.S. Pat. No. 7,037,669, 2006.
9. Hu et al. U.S. Pat. No. 5,328,828 "Compositions and methods for determining the presence of amphetamines in sample suspected of containing amphetamine and/or methamphetamine" Issued: Jul. 12, 1994.
10. Hu et al. U.S. Pat. No. 5,135,863 "Compositions and methods for determining the presence of amphetamines in sample suspected of containing amphetamine and/or methamphetamine" Issued: Aug. 4, 1992.
11. Lin et al. U.S. Pat. No. 7,560,239 "Homogeneous enzyme immunoassay for simultaneous detection of multiple analytes" Issued: Jul. 14, 2009.
12. Lee, W. T., et al, "Cloning of the gene and amino acid sequence for glucose 6-phosphate dehydrogenase from *Leuconostoc mesenteroides*." J. Biol. Chem., 266(20), 13028-13034 (1991)
13. Uniprot, [P11411] RecName: Full=Glucose-6-phosphate 1-dehydrogenase; Short=G6PD; EC=1.1.1.49;
14. Swissprot [P11411] RecName: Full=Glucose-6-phosphate 1-dehydrogenase; Short=G6PD; EC=1.1.1.49.

We claim:

1. A method for producing a composition, the composition comprising at least a first specific binding pair (first-sbp) member and a second specific binding pair (second-sbp) member conjugated to a mutated glucose-6-phosphate dehydrogenase (G6PDH), wherein the first specific binding pair member is distinct from the second specific binding pair member and wherein the mutation of the mutated glucose-6-phosphate dehydrogenase (G6PDH) comprises the insertion of at least one cysteine or substitution of at least one amino acid with cysteine and wherein the first specific binding pair member is conjugated to said mutated G6PDH via the thiol group on the cysteine and the second specific binding pair member is conjugated to said G6PDH via an amino group on the mutated G6PDH, the method comprising the steps of:
    conjugating the first specific binding pair member to the mutated G6PDH via the thiol group of the cysteine to provide a mutated G6PDH-first-sbp member conjugate; and then
    conjugating the second specific binding pair member to the mutated G6PDH-first-sbp member conjugate via an amino group on mutated G6PDH of the mutated G6PDH-first-sbp member conjugate.

2. The method according to claim 1, wherein the step of conjugating includes providing a linker between G6PDH and either or both of specific binding pair member and further specific binding pair member.

3. The method of claim 1, wherein G6PDH is a bacterial G6PDH derived from the genus of *Leuconostoc*.

4. The method of claim 1, wherein the first specific binding pair member and the second specific binding pair member are serologically not cross-reactive.

5. The method of claim 1, wherein the composition comprises three or more distinct specific binding pair (sbp) members conjugated to the mutated G6PDH.

6. The method of claim 1, wherein the composition comprises a plurality of distinct further specific binding pair members conjugated to a respective plurality of amino groups on the mutated G6PDH.

7. The method of claim 1, wherein the composition comprises a plurality of distinct first specific binding pair members conjugated to a respective plurality of thiol groups on the mutated G6PDH.

8. The method of claim 1, wherein the first and the second specific binding pair members are selected from the group consisting of opium, opioid analgesics, amphetamines, cocaine, methadone, alkaloids, catecholamines, methylendioxyamphetamines (MDMA, MDA, and MDEA, etc.), PCP, propoxyphene, methaqualone, barbiturates, benzodiazepines, tricyclic antidepressants, tranquilizers, tetrahydrocannabinol, LSD, ketamine, GHB, , including amino acids, hormones, steroids, buprenorphine, norbuprenorphine, and analogs, metabolites, and derivatives thereof.

9. The method of claim 1, wherein the first specific binding pair member and the second specific binding pair member are serologically not cross-reactive.

* * * * *

SEQUENCE LISTING

<160> NUMBER OF SEQ ID NOS: 1

<210> SEQ ID NO 1
<211> LENGTH: 485
<212> TYPE: PRT
<213> ORGANISM: Leuconostoc mesenteroides

<400> SEQUENCE: 1

Val Ser Glu Ile Lys Thr Leu Val Thr Phe Phe Gly Gly Thr Gly Asp
1               5                   10                  15

Leu Ala Lys Arg Lys Leu Tyr Pro Ser Val Phe Asn Leu Tyr Lys Lys
            20                  25                  30

Gly Tyr Leu Gln Lys His Phe Ala Ile Val Gly Thr Ala Arg Gln Ala
        35                  40                  45

Leu Asn Asp Asp Glu Phe Lys Gln Leu Val Arg Asp Ser Ile Lys Asp
    50                  55                  60

Phe Thr Asp Asp Gln Ala Gln Ala Glu Ala Phe Ile Glu His Phe Ser
65                  70                  75                  80

Tyr Arg Ala His Asp Val Thr Asp Ala Ala Ser Tyr Ala Val Leu Lys
                85                  90                  95

Glu Ala Ile Glu Glu Ala Ala Asp Lys Phe Asp Ile Asp Gly Asn Arg
            100                 105                 110

Ile Phe Tyr Met Ser Val Ala Pro Arg Phe Phe Gly Thr Ile Ala Lys
        115                 120                 125

Tyr Leu Lys Ser Glu Gly Leu Leu Ala Asp Thr Gly Tyr Asn Arg Leu
    130                 135                 140

Met Ile Glu Lys Pro Phe Gly Thr Ser Tyr Asp Thr Ala Ala Glu Leu
145                 150                 155                 160

Gln Asn Asp Leu Glu Asn Ala Phe Asp Asn Gln Leu Phe Arg Ile
                165                 170                 175

Asp His Tyr Leu Gly Lys Glu Met Val Gln Asn Ile Ala Ala Leu Arg
            180                 185                 190

Phe Gly Asn Pro Ile Phe Asp Ala Ala Trp Asn Lys Asp Tyr Ile Lys
        195                 200                 205

Asn Val Gln Val Thr Leu Ser Glu Val Leu Gly Val Glu Glu Arg Ala
    210                 215                 220

Gly Tyr Tyr Asp Thr Ala Gly Ala Leu Leu Asp Met Ile Gln Asn His
225                 230                 235                 240

Thr Met Gln Ile Val Gly Trp Leu Ala Met Glu Lys Pro Glu Ser Phe
                245                 250                 255

Thr Asp Lys Asp Ile Arg Ala Ala Lys Asn Ala Ala Phe Asn Ala Leu
            260                 265                 270

Lys Ile Tyr Asp Glu Ala Glu Val Asn Lys Tyr Phe Val Arg Ala Gln
        275                 280                 285

Tyr Gly Ala Gly Asp Ser Ala Asp Phe Lys Pro Tyr Leu Glu Glu Leu
    290                 295                 300

Asp Val Pro Ala Asp Ser Lys Asn Asn Thr Phe Ile Ala Gly Glu Leu
305                 310                 315                 320

Gln Phe Asp Leu Pro Arg Trp Glu Gly Val Pro Phe Tyr Val Arg Ser
                325                 330                 335

Gly Lys Arg Leu Ala Ala Lys Gln Thr Arg Val Asp Ile Val Phe Lys
            340                 345                 350

Ala Gly Thr Phe Asn Phe Gly Ser Glu Gln Glu Ala Gln Glu Ala Val
        355                 360                 365

```
Leu Ser Ile Ile Ile Asp Pro Lys Gly Ala Ile Glu Leu Lys Leu Asn
    370             375             380

Ala Lys Ser Val Glu Asp Ala Phe Asn Thr Arg Thr Ile Asp Leu Gly
385             390             395                         400

Trp Thr Val Ser Asp Glu Asp Lys Lys Asn Thr Pro Glu Pro Tyr Glu
                405             410                     415

Arg Met Ile His Asp Thr Met Asn Gly Asp Gly Ser Asn Phe Ala Asp
                420             425             430

Trp Asn Gly Val Ser Ile Ala Trp Lys Phe Val Asp Ala Ile Ser Ala
        435             440             445

Val Tyr Thr Ala Asp Lys Ala Pro Leu Glu Thr Tyr Lys Ser Gly Ser
    450             455             460

Met Gly Pro Glu Ala Ser Asp Lys Leu Leu Ala Ala Asn Gly Asp Ala
465             470             475             480

Trp Val Phe Lys Gly
            485
```